(12) United States Patent
Deck et al.

(10) Patent No.: US 12,194,273 B2
(45) Date of Patent: Jan. 14, 2025

(54) DOSING UNIT REFILLING SCHEDULING

(71) Applicant: Roche Diabetes Care, Inc., Indianapolis, IN (US)

(72) Inventors: Frank Deck, Mannheim (DE); Stefan Pfalz, Mannheim (DE); Hans List, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1133 days.

(21) Appl. No.: 16/999,356

(22) Filed: Aug. 21, 2020

(65) Prior Publication Data
US 2020/0376189 A1 Dec. 3, 2020

Related U.S. Application Data

(63) Continuation of application No. PCT/EP2019/053005, filed on Feb. 7, 2019.

(30) Foreign Application Priority Data

Feb. 23, 2018 (EP) ..................... 18158365

(51) Int. Cl.
*A61M 5/142* (2006.01)
*A61M 5/14* (2006.01)
*A61M 5/168* (2006.01)

(52) U.S. Cl.
CPC .......... *A61M 5/142* (2013.01); *A61M 5/1408* (2013.01); *A61M 5/16809* (2013.01);
(Continued)

(58) Field of Classification Search
CPC ................ A61M 5/142; A61M 5/1408; A61M 5/16809; A61M 5/16881;
(Continued)

(56) References Cited

U.S. PATENT DOCUMENTS

2007/0088271 A1 4/2007 Richards
2010/0049127 A1 2/2010 Haueter et al.
(Continued)

FOREIGN PATENT DOCUMENTS

EP 1 970 677 A1 9/2008
EP 2 881 128 A1 6/2015
(Continued)

OTHER PUBLICATIONS

International Search Report and Written Opinion of the International Searching Authority, PCT/EP2019/053005, Jun. 5, 2019, 10 pages.

*Primary Examiner* — Jason E Flick
(74) *Attorney, Agent, or Firm* — Bose McKinney & Evans LLP

(57) ABSTRACT

A method for managing refilling a first reservoir of an ambulatory infusion system from a first container that stores a first drug and for managing refilling a second reservoir of the ambulatory infusion system out of a second container that stores a second drug is disclosed. The method includes repeatedly and automatically carrying out a filling volume assessment routine, which involves determining the expected infusion of the first drug and the second drug between the present time $t_p$ and the end of an estimation time interval $t_f$ and determining if the first reservoir shall be refilled and/or if the second reservoir shall be refilled at $t_p$ based on the expected infusion of the first drug and the second drug determined in step (a). Ambulatory infusion device control units and ambulatory infusion devices that are configured for carrying out such method are also disclosed.

12 Claims, 3 Drawing Sheets

(52) U.S. Cl.
CPC ............... *A61M 5/16881* (2013.01); *A61M 2005/14208* (2013.01)

(58) Field of Classification Search
CPC .... A61M 2005/14208; A61M 5/16827; A61M 5/1407; A61M 5/1413
See application file for complete search history.

(56) References Cited

U.S. PATENT DOCUMENTS

| | | | |
|---|---|---|---|
| 2012/0053514 A1* | 3/2012 | Robinson ............ | A61M 5/1684 604/246 |
| 2015/0100038 A1 | 4/2015 | McCann et al. | |
| 2015/0133888 A1* | 5/2015 | Ali .................... | A61M 5/16877 604/503 |
| 2016/0317741 A1* | 11/2016 | List .................... | A61M 5/1413 |

FOREIGN PATENT DOCUMENTS

| | | |
|---|---|---|
| JP | H 07-51385 A | 2/1995 |
| JP | 5908969 B2 | 4/2016 |
| JP | 2016-536039 A | 11/2016 |
| JP | 2016-538958 A | 12/2016 |
| WO | WO 2012/140063 A1 | 10/2012 |
| WO | WO 2015/070161 A1 | 5/2015 |
| WO | WO 2017/040928 A1 | 3/2017 |

\* cited by examiner

DOSING UNIT REFILLING SCHEDULING

RELATED APPLICATIONS

This application is a continuation of PCT/EP2019/053005, filed Feb. 7, 2019, which claims priority to EP 18 158 365.9, filed Feb. 23, 2018, the entire disclosures of both of which are hereby incorporated by reference herein.

BACKGROUND

The present disclosure relates to infusion devices and infusion systems for the combined infusion of two or more drugs. It particularly relates to scheduling the filling of one more reservoirs (which may also be called "secondary reservoirs") out of containers (which may also be called "primary reservoirs") for subsequent infusion out of the one or more reservoirs over an extended time period. A typical field of application is diabetes therapy by way of combined insulin and glucagon infusion.

Ambulatory infusion devices are well known in the art for example in the therapy of Diabetes Mellitus by Continuous Subcutaneous Insulin Infusion (CSII) as well as in pain therapy or cancer therapy and are available from a number of suppliers. Throughout this document, a design that is particularly suited for CSII is generally assumed for exemplary purposes.

Ambulatory infusion devices that are used for CSII are designed to be carried by a Person with Diabetes (PwD), also referred to as "user," generally continuously night and day. The devices are designed to be carried concealed from view, e.g., with a belt clip or in a pocket, and/or may be designed to be alternatively carried directly attached to the body via an adhesive pad. Ambulatory infusion devices are designed to infuse drug, in particular insulin, in at least two ways. First, they are designed to infuse drug substantially continuously according to a typically pre-programmed and time variable basal infusion schedule autonomously, i.e., without requiring particular user interactions or operations. Second, they are designed to infuse larger drug boli on demand, for example to compensate for the intake of carbohydrates as well as to correct undesired high blood glucose values. To control these and optional further functions, ambulatory infusion devices comprise an electronics control unit, typically based on one or more microprocessors in particular, microcontrollers. Throughout this document, the expressions "ambulatory infusion device" and "ambulatory infusion system" refer to a device and system respectively with at least the before-described basic functionality. The terms "control unit" and "controller" are used interchangeably herein. "Respectively" is used in this specification in some instances to mean "in particular."

According to a classic and well-established design, ambulatory infusion devices or systems are typically of the syringe-driver type where drug is infused out of a drug cartridge by way of controlled and incremental displacement of a cartridge piston. For displacing the cartridge piston, a spindle drive with an electric motor is provided. Typical cartridge volumes are in a range of, e.g., 1 ml to 3 ml and store drug, in particular insulin, for a number of days up to a week or more. A number of drawbacks of such devices are known in the art. In particular, they have a limited precision because they involve delivering very small drug amounts, typically in the nanoliter range, out of a drug cartridge having an overall drug volume in the milliliter range. Therefore, additional concepts and architectures have been proposed which use a dedicated dosing unit downstream from the drug reservoir, comprising, e.g., a micro membrane pump or a micro piston pump and are adapted to couple to a drug reservoir and especially designed for precise metering of small volumes. While several designs for such dosing units are known in the art, they are rather complex, and most of them are expensive and/or critical with respect to large scale.

U.S. Publication No. 2010/049127 A1, incorporated herein by reference in its entirety, discloses a system with a miniaturized metering piston pump with a dosing cylinder that is repeatedly fluidically coupled to and filled from a larger reservoir, followed by fluidically coupling the dosing cylinder to an infusion site and infusing the drug out of the dosing cylinder in incremental steps and over an extended time period. For alternatively coupling the dosing cylinder to the reservoir and the infusion site, a valve system or valve unit is proposed. The infusion is a metered infusion of controlled volumes respectively volume increments.

Throughout the document, an architecture in accordance with the principles of U.S. Publication No. 2010/049127 A1 is assumed, where not stated differently. The larger reservoir is also referred to as "container" and stores drug for a number of days up to a week or more as explained before. The inner volume of the dosing cylinder is referred to as "reservoir." Out of the dosing cylinder, drug is infused in substantially the same way as in the case for the above-described classic syringe-driver design. Both the valve switching and the displacement of a piston in the reservoir, and the valve switching are controlled by way of an electronic control unit.

In contrast to a classic syringe-driver, the filling volume of the reservoir is comparatively small and may, by way of example, be 70 microliters, corresponding to 7 IU (International Units) of a liquid insulin formulation of standard concentration U100.

Whenever the reservoir is empty or approaching emptiness, refilling out of the container is required for continuing the infusion. Monitoring the filling state of the reservoir and refilling it as required is favorably a background process that is controlled and executed by the ambulatory infusion device autonomously, without requiring user involvement. For a number of reasons and constraints related to the device design and energy consumption, the filling and refilling of the reservoir is favorably carried out comparatively slowly and may require a time in a range of, e.g., 1 minute or more.

WO 2012/140063 A1 discloses an ambulatory infusion device and a method for operating such device which includes the steps of: (a) determining a maximum refill level for the reservoir, based on given external parameters, wherein the maximum refill level does not exceed the maximum capacity of the reservoir; (b) filling the reservoir with liquid medicament from the container to the maximum refill level; (c) metering and conveying the multitude of portions of liquid medicament to the downstream conduit; (d) if the reservoir becomes empty, refilling the reservoir as in step (b) and continuing with step (c).

The hormone glucagon is an insulin antagonist that allows quickly raising the diabetic's blood glucose. While the injection of glucagon is a routine measure in the emergency treatment of PwDs that undergo a severe hypoglycemia, glucose is not routinely used in regular diabetes treatment. However, the infusion of both the hormones insulin and its antagonist glucagon may improve the therapy quality.

Ambulatory infusion devices have accordingly been proposed that allow for the infusion of both insulin and glucagon, essentially using two separate syringe driver pumps. Such devices, however, are complex, bulky and expensive.

At present, no devices and systems are commercially available that would be suited for routine use.

Apart from the infusion of insulin and glucagon in diabetes therapy, a generally similar situation is present where the combined administration of two or more drugs over an extended period of time is desirable, for example in various hormone therapy, cancer therapy or pain therapy. Throughout this document, the infusion of insulin and glucagon is primarily considered for exemplary purposes, without excluding other drugs additionally or alternatively.

In the context of insulin and glucagon infusion for diabetes therapy, insulin infusion generally includes both basal and bolus infusion as explained before, while glucagon is typically bolus infusion only that is carried out in particular situations. In the following, such application is generally assumed where not stated differently. Further, for the case of insulin and glucagon infusion, insulin is considered as the first drug and glucagon is considered as the second drug.

In the context of an ambulatory infusion device and ambulatory infusion system with a container and a reservoir as explained before, unnecessary refilling steps should generally avoided since each refilling is associated with considerable energy consumption and potentially the introduction of some dosing error because of the valve switching and directional changes of the piston movement. Further, it is desirable to infuse drug boli, as far as possible, without the need to refill the reservoir in between. That is, a refilling of the reservoir during the bolus infusion should be avoided.

SUMMARY

The present disclosure provides an ambulatory infusion device and ambulatory infusion system that are generally based on the use of two or more containers with different drugs in combination with one or more reservoirs. The drugs are liquid drugs.

The present disclosure teaches a method of managing and scheduling the filling or refilling of the one or more reservoirs such that refilling occurs at suitable points in time. Particularly suitable points in time are such times where the therapeutically relevant operation of the ambulatory infusion device, in particular the basal and bolus infusion, is not affected, or the effect is at least small. Favorably, unnecessary refilling procedures are avoided.

In a general way, managing the reservoirs is achieved by forecasting respectively predicting the volume of the two or more drugs that is expected to be infused in the nearer future and determining the points in time for the refilling based on said prediction.

In the following, the infusion of two different drugs is generally assumed which are referred to as first drug and second drug, respectively. For exemplary purposes, the first drug is a liquid insulin formulation and the second drug is a liquid glucagon formulation.

In an aspect, a method is disclosed for scheduling a refilling of a first reservoir of an ambulatory infusion system out of a first container storing a first drug and for scheduling the refilling of a second reservoir of the ambulatory infusion system out of a second container storing a second drug. The second container is distinct from the first container. The method further includes repeatedly and automatically carrying out a filling volume assessment routine, the filling volume assessment routine including: determining, at a present point in time, if the first reservoir shall be refilled and/or if the second reservoir shall be refilled, the determination being based on expected infusion of first drug and second drug between the present point in time ("$t_p$") and a future estimation point in time ("$t_f$").

Via the method, it is determined whether the first and/or second reservoir should be refilled immediately, in particular, at the present point in time in order to avoid the need for refilling at a potentially unsuited future point in time, in particular, at a point in time where drug administration shall be carried out and the remaining filling volume of the reservoir is likely to be insufficient.

The method is typically computer-implemented and is executed by way of one or more microcomputer(s) and/or microcontroller(s) that execute(s) corresponding software or firmware code.

In a type of embodiment, the first reservoir is physically distinct from the second reservoir, with the first container being fluidically coupled to the first reservoir and with the second container being fluidically coupled to the second reservoir only.

In other embodiments, however, the first reservoir and the second reservoir are formed by a single common reservoir, the common reservoir alternately serving as first reservoir and as second reservoir. For such type of embodiment, the common reservoir is the only reservoir and may be alternately filled with first liquid drug for the infusion of first liquid drug or with second liquid drug for the infusion of second liquid drug. At a specific point in time, the common reservoir may be filled only with either of the first drug and accordingly serve as first reservoir, or may be filled with the second drug and accordingly serve as second reservoir. Where not explicitly stated differently, the terms "first reservoir" and "second reservoir" may refer to a single common reservoir that serves as first reservoir or second reservoir in a specific context. Further, the first reservoir and the second reservoir may be referred to as "reservoir" only where it is unambiguous.

It is noted that, in addition to a first reservoir and a second reservoir, further reservoirs may be present in an analogous way, either as further physically distinct reservoirs or as a shared common reservoir. For each reservoir, a physically distinct container is present.

The expected infusion is determined based on infusion estimators as estimators for the amount of first drug and second drug between the present point in time and the future point in time.

The time interval between a reference point in time, e.g., the present point in time, and a subsequent point in time, e.g., the future point in time, for which the estimation is carried out, is referred to as estimation time interval. The estimation time interval is a time interval for which the administration of a drug (first, second, or any further) out of a reservoir can be predicted, in particular, estimated with sufficient certainty as explained further below in more detail. It is noted, however, that a precise prediction is not necessary since a reservoir may be refilled out of a container at any time, if required. In the context of diabetes therapy, the estimation time interval may, e.g., be 2 hours. Longer or shorter time intervals, such as 1 hour, or 4 hours, may be used as well. Typically, the estimation time interval is pre-determined and constant. In further embodiments, however, the estimation time interval is not pre-determined but adaptive. As a general rule, the estimation time interval may be long if the predictability is high, that is, if the profile of basal and/or bolus infusion as a function of time of day is constant or similar over an extended time period of, e.g., a number of days or weeks. If the predictability, in contrast, is low, shorter estimation time intervals may be favorable. In an embodiment, the method includes repeatedly determining the variability of the profile of past basal and/or bolus infusion by way of statistical analysis and modifying the estimation time interval in dependence of the determined variability.

In some embodiments, the method includes carrying out the filling volume assessment routine at time intervals of a duration that is shorter than the estimation time interval. The filling volume assessment routine may be carried out with a fixed time interval of, e.g., 10 minutes. Longer or shorter time intervals, such as 5 minutes, 30 minutes, or 60 minutes may also be used. In typical embodiments, the steps are carried out at pre-determined specific times of day under control of a clock circuitry of an ambulatory infusion device. In alternative embodiments, the times of day at which the filling volume assessment routine is carried out are, at least partly, not predetermined but different for different times of day. As a general rule, the filling volume assessment routine may be carried out less often at times of day where the predictability of the basal and/or bolus infusion is high and more often at times of day where the predictability is low. By way of example, the filling volume assessment routine may be carried out more often during daytime and less often during night time. Further, the filling volume assessment routine may optionally be synchronized with the basal infusion, in particular basal insulin infusion. For ambulatory infusion devices with substantially continuous basal insulin infusion in incremental doses as explained further below, it may, e.g., be generally carried out substantially subsequent to an incremental basal infusion, thereby ensuring a maximum available time interval for the refilling of the reservoir and consequently avoiding interference with the next following incremental infusion.

Alternatively or preferably additionally to carrying out the filling volume assessment routine according to a schedule, the method may include carrying out the filling volume assessment routine upon occurrence of a trigger event. Such trigger event may, e.g., be a temporary user-commanded modification of the pre-determined basal infusion schedule or the cancelling of such modification, and/or the occurrence of a therapy-related event which has impact on the infusion, such as a situation of low blood glucose as explained further below in more detail. Further, the programming of an on-demand bolus infusion may serve as trigger event.

The filling volume assessment routine is a background-routine that is carried out with a time-interval, as discussed before, during regular operation of the ambulatory infusion system where basal and/or bolus infusions are carried out. The points in time where the filling volume assessment routine is carried out are current points in time.

In some embodiments, the filling volume assessment routine includes determining a first estimated filling volume of the first reservoir at the future estimation point in time and determining if the first reservoir shall be refilled depending on the first estimated filling volume.

The first estimated filling volume is a predicted filling volume and is the filling volume of the first reservoir that is to be expected at the estimation point in time if drug is infused out of the reservoir from the present point in time to the estimation point in time without the first reservoir being refilled. The same may be applied to the second reservoir or any further reservoir additionally or alternatively in an analogous way.

In some embodiments, the filling volume assessment routine includes determining that the first reservoir shall be refilled if the first estimated filling volume is below a first filling volume threshold. Typically, the first filling volume threshold is pre-determined. In some embodiments of this type, the first filling volume threshold is zero. That is, it is determined that the first reservoir should be refilled at the present point in time if the estimated first filling volume is negative. In this context, it is to be understood that a negative physical filling volume is impossible for technical reasons. Alternatively, a filling volume threshold is not zero but positive and considers, e.g., some safety margin. In such embodiment, a filling volume threshold may, for the case of CSII, e.g., be in a range of 10 microliters to 50 microliters, respectively 1 IU to 5 IUs (International Units) of a liquid insulin formulation of standard concentration U100. A positive filling volume threshold may in particular correspond at least to a back-dosing volume as explained further below. The same principles may be applied to the second reservoir or any further reservoir additionally or alternatively in an analogous way.

In some embodiments, the method includes, as part of the filling volume assessment routine, determining that a reservoir shall not be refilled if the estimated filling volume is below the filling volume threshold, but an expected duration to a next following administration of an on-demand bolus exceeds a bolus timeout threshold. For this type of embodiment, the reservoir may not be refilled at the present point in time even though it should in principle be refilled based on the estimation as explained before. In particular, the reservoir is not refilled for this type of embodiment if the time interval from the present point in time to the predicted or expected point in time for the next on-demand bolus exceeds the bolus timeout threshold. The bolus timeout threshold is typically pre-determined and may, e.g., be 20 min according to a specific example. This type of embodiment avoids a refilling that may, in fact, be unnecessary due to typical variability in drug infusion. In particular, the bolus timeout threshold corresponds to a time interval beyond which the estimated filling volume of the reservoir has a significant likelihood of substantially deviating and being, in particular, above the estimated filling volume. Typical reasons for such deviation may be that basal infusion is temporarily reduced or suspended because of a sportive activity or low blood glucose. Further, if there is a long time to the next bolus as expected, there is some likelihood that the bolus will, in fact, not be infused as expected.

In some embodiments of the before-described type, the method includes, as part of the filling volume assessment routine, determining that the reservoir shall not be refilled if the estimated filling volume is below the filling volume threshold, the expected duration to the next following administration of an on-demand bolus does not exceed the bolus timeout threshold, but an expected bolus volume of the next following on-demand bolus does not exceed a bolus volume threshold. In a situation where the estimated filling volume is below the filling volume threshold and the expected duration to the next following administration of an on-demand bolus does not exceed the bolus timeout threshold, the reservoir should generally be refilled as explained before. For the here-described type of embodiment, however, the reservoir is not refilled under these conditions if the expected bolus volume of the next following on-demand bolus does not exceed the bolus volume threshold. In a typical embodiment, the bolus volume threshold corresponds to the filing level of the reservoir at the present point in time, optionally including a safety margin. The safety margin may at least correspond to a back-dosing volume. For this type of embodiment, the reservoir is not refilled at the present point in time if it can be expected that the filling volume without prior refilling is sufficient for the administration of the next following on-demand bolus.

In some embodiments, the filling volume assessment routine includes determining the first estimated filling volume by subtracting a first infusion estimator, the first infusion estimator being an estimator for the amount of drug that is expected to be infused between the present point in time and the future estimation point in time, from a first filling volume of the first reservoir at the present point in time. The first infusion estimator may include a dedicated basal infusion estimator and a dedicated bolus infusion estimator for combined basal and bolus infusion, as explained further below where both basal and bolus infusion occurs for the drug, e.g., for insulin in diabetes therapy. Further, the infusion estimator may be a combined infusion estimator that reflects the total infusion, both bolus and basal. The same principles may be applied to the second reservoir or any further reservoir additionally or alternatively in an analogous way.

In some embodiments, the method includes computing a set of first standard infusion estimators, with each first standard infusion estimator being an estimator for an amount of first drug that is expected to be infused in an estimation time interval beginning at an associated pre-determined time of day, and storing the set of first standard infusion estimators in a memory. For such embodiments, the filling volume assessment routine includes retrieving from the memory the first standard infusion estimator that is associated with the time of day corresponding to the present point in time.

In some embodiments, the method includes computing a set of second standard infusion estimators, with each second standard infusion estimator being an estimator for an amount of second drug that is expected to be infused in an estimation time interval beginning at an associated pre-determined time of day, and storing the set of second standard infusion estimators in a memory. For such embodiments, the filling volume assessment routine includes retrieving from the memory the second standard infusion estimator that is associated with the time of day corresponding to the present point in time.

The retrieved standard infusion estimator at the present point in time is used as infusion estimator for the prediction. By way of example, standard infusion estimators may be computed with a time interval of ten minutes, e.g., for 0:00 (midnight), 0:10, 0:20, 0:30, 0:40, 0:50, 1:00 (1 am), and so forth. The times of day at which the filling volume assessment routine is carried out are also referred to assessment times of day in the following.

The standard infusion estimators are favorably pre-computed and do not need to be computed as part of the repeatedly carried out filling volume assessment routine, with the determining and storing of the set of standard infusion estimators forming an infusion estimation routine. However, the infusion estimation routine may be carried out occasionally or periodically, thereby updating or re-computing the set of standard infusion estimators. Typically, the standard infusion estimators consider both basal and bolus infusion where both basal and bolus infusion occurs for the drug, e.g., for insulin in diabetes therapy. Each standard infusion estimator from the set of standard infusion estimators may include a standard basal infusion estimator and/or a standard bolus infusion estimator as explained in more detail further below. Alternatively, however, an infusion estimator may be explicitly computed as part of the filling volume assessment routine each time the filling volume assessment routine is carried out. The same principles for the computation of standard infusion estimators may be applied to the second reservoir or any further reservoir additionally or alternatively in an analogous way.

In some embodiments, determining if the first reservoir shall be refilled is based, at least in part, on a pre-determined first basal infusion schedule for the first drug.

In therapies that include a substantially continuous drug infusion, such as insulin infusion, basal drug infusion is normally carried out in accordance with a basal infusion schedule. The basal infusion schedule is generally pre-determined and time-variable, that is, the rate of basal infusion varies as a function of time. Typically, but not necessarily, the basal infusion schedule is, in CSII, a cyclic circadian schedule, having a period of 24 hours. In such case, assumed in the following for exemplary purposes where not stated differently, the rate of basal infusion is accordingly defined in dependence of the time of day. Typically, the basal infusion schedule is stored in a memory of an ambulatory infusion system, in particular an ambulatory infusion device control unit, by way of a lookup table that comprises the basal infusion rate for time intervals, e.g., for each hour of day or each half hour of day. It is further noted, that, in a practical implementation, basal infusion is often not carried out in a continuous manner in a strict sense, but in incremental doses, with a fixed time interval of, e.g., 3 minutes or six minutes between successive incremental doses. Alternatively, the incremental dose is fixed to, e.g., 0.05 IU, 0.1 IU or 0.2 IU and the time interval between successive doses is varied in accordance with the basal infusion schedule. In a further variant, a mixture or combination of both before-mentioned approaches is used. Further, the basal infusion schedule may not be stored in the form of a lookup table, but in form a mathematical function, in particular, the parameters of such function. While it may be temporarily suspended or modified by a user as explained further below, basal administration is generally carried out by an ambulatory infusion system autonomously under control of an ambulatory infusion device control unit, without requiring user interaction.

Determining the estimated filling volume, based, at least in part, on a pre-determined basal infusion schedule includes determining the total amount (volume) of basal infusion for the estimation time interval and subtracting this value from the filling volume of the reservoir at the present point in time. The total amount of basal infusion that is determined in accordance with the pre-determined basal infusion schedule serves as basal infusion estimator.

Since the basal infusion schedule is generally pre-determined, the basal infusion estimator may be pre-computed in an infusion estimation routine as mentioned before. In particular, for a given start time of day and a given end time of day, a standard basal infusion estimator may be computed by summing up respectively integrating the volume of basal infusion in accordance with the basal infusion schedule for the time interval between the start time of day end the end time of day. Here, computing the estimated filling volume as part of the filling volume assessment routine simply comprises retrieving from the memory the standard basal infusion estimator in accordance with the present point in time, and subtracting this value from the filling volume of the reservoir at the present point in time. Computing the standard basal infusion estimators may, for example, be carried out each time the basal infusion schedule is reprogrammed or each time the reservoir is replaced. It may in particular be carried out along with computing bolus infusion estimators as explained further below.

The basal infusion schedule being pre-determined means that it is generally stored and accordingly known in advance as explained before. Typically, the basal infusion schedule is programmed in accordance with the patient's individual needs by a healthcare professional or in some cases by the patient as required, and may be reprogrammed if needed. Because the basal infusion schedule is generally pre-determined, the prediction of the filling volume of the reservoir is correct, provided that basal infusion is actually carried out in accordance with the schedule. As discussed further below in more detail, this is not necessarily the case.

In some embodiments, determining the estimated filling volume includes taking into account temporary modifications of the pre-determined basal infusion schedule in a time interval between the present point in time and the estimation point in time. A temporary modification of the basal infusion schedule may typically occur spontaneously and at any point in time. State-of-the-art ambulatory infusion systems allow a user to temporarily modify basal infusion for a time interval of typically a number of hours, e.g., up to, for example, 12 hours or 24 hours, in order to cope with special or exceptional circumstances such as sportive activities or illness, and/or to temporarily suspend basal infusion. A temporarily applied basal infusion schedule that results from such modification is referred to as a modified basal infusion schedule. In dependence of the ambulatory infusion system, the modified basal infusion schedule may be determined by proportional scaling of the basal infusion according to the pre-determined schedule with a scaling factor that may be larger than one (for increased basal infusion) or smaller than one (for decreased basal infusion). In a further variant, the modified basal infusion schedule is determined as constant basal rate infusion schedule with the pre-determined basal infusion schedule being temporarily replaced by the constant basal rate infusion schedule. Taking into account temporary modifications of the pre-determined basal infusion schedule is achieved by replacing or modifying the pre-determined basal infusion schedule with the modified basal infusion schedule for the estimation time interval or a part of the estimation time interval where the modification is active. As mentioned before, the programming or ending of the temporary modification may serve as a trigger event that forces the filling volume assessment routine to be carried out immediately, typically asynchronous with the general schedule. The same holds true for temporary modifications based on measured and/or predicted blood glucose values as explained below.

In some embodiments, the method includes taking into account a measured and/or predicted blood glucose level for predicting the estimated filling volume. This type of embodiment is particularly favorable in the context of CSII. The ambulatory infusion system may include or be designed to operatively couple with a continuous glucose measurement unit that is designed to measure glucose concentration in a body fluid or body tissue in a substantially continuous way. The ambulatory infusion system may further be designed to temporarily modify the basal infusion schedule in accordance with the measured blood glucose value. It may, in particular, be designed to temporarily suspend basal infusion or reduce basal infusion according to the pre-determined threshold in case of low blood glucose values. Such modification of the basal infusion schedule results in a modified basal infusion schedule as explained before in the context of user-commanded modifications and can be considered in an analogous way.

It is to be understood that a temporary modification of the basal infusion schedule may have a typically user-programmed and pre-determined duration that is, e.g., selected in accordance with a planned physical activity. In embodiments where the basal infusion estimator is generally pre-computed as explained above, correspondingly modified basal infusion estimators that take into account the temporary modification may be computed at the beginning of the modification for the time span that covers the upcoming estimation points in time that are affected by the modification as programmed. The volume assessment may then use the modified basal infusion estimators for the affected time span.

Alternatively, however, the duration of the temporary modification may not be known in advance. This may in particular be the case if the temporary modification is controlled by a continuous glucose measurement unit as explained before. Here, taking into account temporary modifications of the pre-determined basal infusion schedule may be achieved by determining, in the volume assessment routine, if a modification is active at the present point in time and using, in the affirmative case, a correspondingly modified basal infusion estimator. For this type of embodiment, the modified basal infusion estimator is accordingly computed at the present point in time, rather than at the beginning of a modification interval. It is noted that this kind of embodiment may also be used even if the duration of the modification is known. It is further noted that typically an active modification may be cancelled by the user. In this case, operation favorably proceeds based on the pre-determined basal infusion schedule.

In some embodiments, determining if the first reservoir shall be refilled is based, at least in part, on an expected amount of on-demand bolus infusion for the first drug between the present point in time and the future estimation point in time.

In the context of CSII, on-demand boli of insulin, as an exemplary first drug, are infused in order to compensate for the intake of food, in particular carbohydrates, and additionally in order to correct undesired high blood glucose values. In contrast to the basal infusion, on-demand boli are generally initiated or triggered via a dedicated user command at any point in time and may have a varying amount. On-demand boli are typically infused within a comparatively short time interval in a typical range from seconds or fractions of a second, up to a few minutes. To cope with special situations, such as the ingestion of some type of foodstuff, an on-demand bolus may also be infused over a longer time period of, e.g., an hour, up to several hours, and/or may be a combination of a portion that is infused substantially immediately and a further portion that is infused over a longer time period. Typical state-of-the-art infusion devices as used, e.g., in CSII typically offer a number of pre-defined bolus profiles (referred to, for example, as Multi Wave Bolus, Extended Bolus, etc.) from which the user may select as required in a specific situation.

Because of their typical variability in amount and size, the prediction of on-demand boli is less straight-forward as compared to the prediction of basal infusion. In practical application scenarios, for example in CSII, however, some predictability is typically given. Since meals often tend to be ingested at similar points in time for different days and further often tend to be similar in size and/or composition, on-demand boli also tend to be similar.

Determining the estimated filling volume, based, at least in part, on an expected amount respectively volume of on-demand bolus infusion may include determining an expected total bolus volume from a start time to an end time, and subtracting this volume from the filling volume of the reservoir at the present point in time. As explained before in the context of basal infusion, the time difference between the end time and the start time corresponds to the estimation time interval and the end time is defined by the start time plus the estimation time interval. The expected amount of on-demand bolus infusion serves as bolus infusion estimator for the bolus infusion between the start time and the end time.

Similar to a basal infusion estimator, the bolus infusion estimator may be determined online at the present point, or may be pre-determined. In the latter case, the steps that are carried out at the present point of time and as part of the filling volume assessment routine are reduced to retrieving the corresponding value for the bolus infusion estimator and subtracting it from the filling volume of the reservoir at the present point in time.

The consideration of basal infusion, bolus infusion as well as combined basal and bolus infusion has been described above with focus on insulin infusion as first drug, with a bolus infusion estimator being a first bolus infusion estimator and a basal infusion estimator being a first basal infusion estimator. The same principles may, however, be applied in an analogous way to all drugs for which basal infusion occurs, such as a second, third, etc. and any further drug where applicable.

In some embodiments, predicting the estimated filling volume is based, at least in part, on a history of actual past infusion. A history of actual past infusion is typically stored by a history memory of an ambulatory infusion system and in particular the ambulatory infusion device control unit. Further, a history of actual past infusion may be stored in a structurally separate remote device, such as a remote controller or diabetes management device. The remote device and the ambulatory infusion device control unit are typically configured to communicate and exchange data via corresponding commination interfaces.

In some embodiments, the history of actual past infusion is stored by one or more external devices at one or more remote locations, such as a server or a cloud and are transmitted directly to the ambulatory infusion device and/or a remote controller or diabetes management device as required by way of internet communication. Further, infusion estimators, in particular standard infusion estimators may be pre-computed and stored by such external device(s).

In some embodiments, a history stores the time and amount of each drug infusion, be it the infusion of an on-demand bolus or an incremental basal infusion in accordance with the basal infusion schedule, together with a time stamp (the time stamp providing information regarding the time of day and favorably also the date). Since, however, basal administration is generally carried out according to a pre-determined basal infusion schedule and at pre-determined points in time (such as every three minutes, starting at 0:00), the history of past basal infusion can be determined from the basal infusion schedule, provided that no events have occurred which temporarily influence the basal infusion.

The history of on-demand boli is stored by way of a list of time stamps and bolus volumes $(t_i, B_i)$, with i being an index value, $t_i$ being the time stamp of a past bolus infusion and $B_i$ being the corresponding bolus volume. If the ambulatory infusion device offers different types of on-demand boli as explained before, further relevant data such as an identifier of the bolus type, the volumes which are infused immediately and over the longer time period as well as the time period over which the infusion is carried out, are stored.

A history of actual past infusion is particularly favorable for determining a bolus infusion estimator as explained before. A bolus infusion estimator for a given start time as time of day may be obtained by way of statistical evaluation of actual past bolus infusions for an interval starting with the start time and ending with the start time plus the estimation time interval as end time. The statistical evaluation may include one or, favorably, a number of days. The determination of the bolus infusion estimator may consider the last preceding days or, favorably, a number of preceding days, such as 7, 14, or 30 days. The determination may be computed each time directly from the volumes of past bolus infusions, or may be computed by respectively modifying a previously computed estimator. In some embodiments, all past days that are used for the computation are weighted equally. In alternative embodiments, however, different days are weighted differently. In particular, days of the recent past may be considered with a higher weight as compared to days of the more distant past.

As bolus infusion estimator, a predetermined percentile of bolus infusion volumes for the considered past days, such as the $80^{th}$ percentile or the $90^{th}$ percentile or $100^{th}$ percentile may be used, with the $100^{th}$ percentile being the maximum bolus infusion volume for the considered past days and time interval from start time to end time. It is noted that other static measures that are known in the art, e.g., based on mean and variance, may be used as well.

In some embodiments, determining the bolus infusion estimator based on a history of actual past infusion for a number of past days considers a continuous sequence of past days. Alternatively, however, only selected days may be considered. For example, bolus infusion estimators may be computed separately for all days or the week, or separately for working days and weekends. Such embodiments may be advantageous in case the typical bolus infusion pattern is substantially different for different days. In further embodiments, a user input may be provided for the exclusion of particular days from the computation, such as days of illness, traveling, or general exceptional circumstances. This type of embodiment is particularly favorable if only a small number of days is used for computation, resulting in the infusion history of each day having significant impact on the computation.

If the bolus infusion estimator is not computed online each time the filling volume assessment routine is carried out, that is, at the present point in time, it may be computed, e.g., once a day, once a week, or along with replacing the reservoir.

It is noted that, similar to computing the bolus infusion estimator separately for different days, basal infusion estimators may be computed separately for different days. Typical state of the art ambulatory infusion systems allow the definition of different basal infusion schedules between which the user may switch or the system may switch automatically, to cope, e.g., with the difference between day shift and night shift, and/or between working days and weekends. Basal infusion estimators may be determined separately for the different basal infusion schedules.

Alternatively to determining a bolus infusion estimator based on a history of actual past infusion as explained before, a bolus infusion estimator may be pre-computed based, e.g., on a diabetic's nutrition schedule and may be stored in a memory of the ambulatory infusion system, e.g., by way of a lookup table for the single times of days at which the determination is carried out, with the single times of days serving as start times.

In a further variant, both of the before-mentioned approaches are combined and bolus infusion estimators are pre-defined, e.g., based on a nutrition schedule, when an ambulatory infusion device is set-up respectively initialized after supply to a user, or in case the nutrition schedule is fundamentally changed. Subsequently, the estimators are amended or modified based on the history of actual past infusion.

In embodiments that include computing a set of standard basal infusion estimators for pre-determined assessment times of day, the set of standard basal infusion estimators may include a basal infusion estimator for each assessment time of day, e.g., for 0:00, 0:10, 0:20, and so forth.

In embodiments that involve computing a set of standard bolus infusion estimators for pre-determined assessment times of day as explained before, a bolus infusion estimator may be computed for each of the assessment times of day, e.g., for 0:00, 0:10, 0:20 and so forth, like for the basal infusion.

A set of pre-computed infusion estimators may accordingly be represented by a table respectively a list of triples, each triple comprising an assessment time of day, $T_j$, a corresponding pre-computed basal infusion estimator $b^*_j$ and a corresponding pre-computed bolus infusion estimator $B^*_j$, with j being an index.

Since on-demand bolus infusion is, however, typically carried out at similar times of day (correlated with the meal times) but with some variability, the method may include determining, from a history of actual past bolus infusions, typical bolus administration times of day and associated typical bolus volumes. Typical bolus administration times of day $\tau_j$ and typical bolus volumes $B^*_j$ may be determined from the history of actual past bolus infusion using statistical or pattern recognition algorithm as—per se—known in the art. The set of typical bolus administration times of day and associated typical bolus volumes may be stored in a list of pairs $(\tau_j, B^*_j)$ that may, e. g., have three to five entries (corresponding to the number of meals/snack) for typical days. When carrying out the filling volume assessment routine at the present point in time, only those typical bolus volumes $B^*_j$ may be considered which lay in the time interval between the present point in time and the future estimation point in time, as indicated by the corresponding typical bolus administration time of day $\tau_j$.

In some embodiments that include determining the estimated filling volume based, at least in part, on an expected amount respectively volume of on-demand bolus infusion, the method may include ignoring selected past boli. In this way, on demand boli that are administered for the purpose of lowering a raised blood glucose value may be excluded for the purpose of the estimation since they are only required sporadically and do typically not follow a defined schedule. For this purpose, a corresponding marker may be stored in a history along with the bolus volume and the time stamp as explained before. Similarly, a bolus may optionally be marked as exceptional for other reasons and also ignored respectively excluded for the computation.

In typical embodiments, both expected basal infusion and expected bolus infusion are considered by subtracting the corresponding amounts from the filling volume at the present point in time. Here, determining, at a present point in time, the estimated filling volume of the reservoir at the future estimation point in time includes subtracting the basal infusion estimator and the bolus infusion estimator from the present filling volume at the present point in time.

The consideration of a history of actual past infusion and the computation of infusion estimators is described primarily with reference to basal and bolus infusion of insulin as the first drug. For the case of the infusion of glucagon as the second drug, the same principles may generally be applied. The infusion of glucagon as second drug, however, may be limited to bolus infusion. Further, the same principles may be applied to a third, fourth and any further drug as applicable.

In some embodiments, the filling volume assessment routine includes determining that the second reservoir shall be refilled if an infusion of second drug is expected to occur between the present point in time and the future estimation point in time and prior to a next following on-demand bolus infusion of the first drug. This type of embodiment is particularly favorable in applications where the first drug is infused most of the time and typically includes basal infusion, while infusion of the second drug occurs only as occasional on-demand bolus infusion. This is the typical case for combined insulin and glucagon infusion with insulin as first drug and glucagon as second drug. Further, this type of embodiment may be favorably used in a setup with a common reservoir as explained before. In a further embodiment, the filling volume assessment routine includes determining that the second reservoir shall be refilled if an infusion of second drug is expected to occur between the present point in time and the future estimation point in time and prior to a next following infusion of the first drug.

In a further aspect, a refilling scheduling unit is disclosed. The refilling scheduling unit is configured to carry out a method for scheduling a refilling of a reservoir according to any embodiment as described before and/or further below. The refilling scheduling unit may be realized by respectively may be based on a microcomputer and/or microcontroller. While a computer-implemented embodiment is further assumed in the following for exemplary purposes, it is not essential. A refilling scheduling unit that is configured to carry out a method in accordance with the present disclosure may also be realized, fully or partly, by other types of circuitry and based, e.g., on an ASIC.

In a further aspect, an ambulatory infusion device control unit is disclosed. The ambulatory infusion device control unit is configured to control operation of an ambulatory infusion device. The ambulatory infusion device control unit includes a first valve control unit, the first valve control unit being configured to control actuation of a first valve actuator to switch a first valve unit between a filling state and an alternative dosing state. The ambulatory infusion device control unit further includes a second valve control unit, the second valve control unit being configured to control actuation of a second valve actuator to switch a second valve unit between a filling state and an alternative dosing state.

The ambulatory infusion device control unit further includes a first reservoir actuator control unit, the first reservoir actuator control unit being configured to control operation of a first reservoir actuator to operate in a filling mode and to increase a fluidic volume of a first reservoir in the filling mode, and to alternatively operate in a dosing mode and to decrease the fluidic volume of the first reservoir in the dosing mode. The ambulatory infusion device control unit further includes a second reservoir actuator control unit, the second reservoir actuator control unit being configured to control operation of a second reservoir actuator to operate in a filling mode and to increase a fluidic volume of a second reservoir in the filling mode, and to alternatively operate in a dosing mode and to decrease the fluidic volume of the second reservoir in the dosing mode.

The ambulatory infusion device control unit further includes a refilling scheduling unit according to any embodiment as discussed above and/or further below. The refilling scheduling unit is configured to operate in parallel with the first reservoir actuator control unit and the second secondary actuator control unit in the dosing mode.

The ambulatory infusion device control unit is further configured, if it is determined that the first reservoir shall be refilled, to control execution of a first reservoir refilling procedure. The first reservoir refilling procedure includes a sequence of: (i) controlling the first valve actuator to switch the first valve unit into the filling state; (ii) controlling the first reservoir actuator to increase the fluidic volume of the first reservoir; (iii) controlling the first valve actuator to switch the first valve unit into the dosing state. The ambulatory infusion device control unit is further configured, if it is determined that the second reservoir shall be refilled, to control execution of a second reservoir refilling procedure, the second reservoir refilling procedure including a sequence of: (i) controlling the second valve actuator to switch the second valve unit into the filling state; (ii) controlling the second reservoir actuator to increase the fluidic volume of the second reservoir; (iii) controlling the second valve actuator to switch the second valve unit into the dosing state.

An ambulatory infusion device control unit according to this type of embodiment is particularly suited in the context of ambulatory infusion devices with a first and second reservoir that are physically distinct from each other, with the first reservoir being fluidically coupled with the first container only and the second reservoir being fluidically coupled with the second reservoir only. Further, for such type of ambulatory infusion device, the first valve actuator and the second valve actuator are physically distinct, with the first valve actuator being coupled with the first valve unit and the second valve actuator being separately coupled with the second valve unit. Further, for such type of ambulatory infusion device, the first reservoir actuator and the second reservoir actuator are physically distinct, with the first reservoir actuator being coupled with and controlling the fluidic volume the first reservoir, and the second reservoir actuator being separately coupled with and controlling the fluidic volume the second reservoir. Due to the separation, the valve switching of the first and second valve unit is generally independent from each other. Similarly, the fluidic volume of the first and second reservoir may be increased or decreased independent from each other.

The fluidic coupling to the patient may either be via a common infusion site interface (e.g., tubing), via fully separate infusion site interfaces for the first and second drug, or via an infusion site interface (tubing) with fluidically distinct separate lumina for the first and second drug.

In a further aspect, a further embodiment of an ambulatory infusion device control unit is disclosed. The ambulatory infusion device control unit is configured to control operation of an ambulatory infusion device. The ambulatory infusion device control unit includes a valve control unit, the valve control unit being configured to control actuation of a valve actuator to switch a valve unit between a first filling state, an alternative second filling state, and an alternative dosing state.

Such further embodiment of an ambulatory infusion device control unit further includes a reservoir actuator control unit. The reservoir actuator control unit is configured to control operation of a reservoir actuator to operate in a filling mode and to increase a fluidic volume of a common reservoir in the filling mode. The reservoir actuator control unit is further designed to alternatively operate in a dosing mode and to decrease the fluidic volume of the common reservoir in the dosing mode.

Such further embodiment of an ambulatory infusion device control unit further includes a refilling scheduling unit according to an embodiment as discussed above and/or further below. The refilling scheduling unit is configured to operate in parallel with the reservoir actuator control unit in the dosing mode.

Such further embodiment of an ambulatory infusion device control unit is further configured, if it is determined that the first reservoir shall be refilled, to control execution of a first reservoir refilling procedure, the first reservoir refilling procedure including a sequence of: (i)(a) controlling the valve actuator to switch the valve unit into the first filling state; (ii)(a) controlling the reservoir actuator to increase the fluidic volume of the common reservoir; (iii)(a) controlling the valve actuator to switch the valve unit into the dosing state.

Such further embodiment of an ambulatory infusion device control unit is further configured, if it is determined that the second reservoir shall be refilled, to control execution of a second reservoir refilling procedure, the second reservoir refilling procedure including a sequence of: (i)(b) controlling the valve actuator to switch the valve unit into the second filling state; (ii)(b) controlling the reservoir actuator to increase the fluidic volume of the common reservoir; (iiib) controlling the valve actuator to switch the valve unit into the dosing state.

In the context of this type of embodiment, the first reservoir and the second reservoir are virtual, while only a single common reservoir is physically present, as explained before. If the common reservoir is filled with the first drug, it serves as first reservoir. If the common reservoir is filled with second drug, it serves as second reservoir.

Since only a common reservoir is present, the coupling to the infusion site interface is realized here via a common tubing respectively a common infusion cannula.

In a particular embodiment of the before-described further embodiment of an ambulatory infusion device control unit, the first reservoir refilling routine includes, prior to step (i)(a), a first emptying sequence, the first emptying sequence including the steps of (i)(a') controlling the valve unit to switch the valve unit into the second filling state; (ii)(a') controlling the reservoir actuator to decease the fluidic of the common reservoir to a minimum volume. Further, the reservoir refilling routine may include, prior to step (i)(b), a second emptying sequence, the second emptying sequence including the steps of (i)(b') controlling the valve unit to switch the valve unit into the first filling state; (ii)(b') controlling the reservoir actuator to decease the fluidic of the common reservoir to a minimum volume.

Since a common reservoir alternatively serves as both first reservoir or second reservoir, emptying the common reservoir from either of the drugs is required before filling or refilling it with the other drug. This is achieved by the before-described first emptying and second emptying sequences. The same principle may be applied for a third, fourth, and generally any number of containers as required.

An ambulatory infusion device control unit according to this further type of embodiment is particularly suited in the context of ambulatory infusion devices with a common reservoir that may alternatively serve as first reservoir or as second reservoir as explained before. Further, for such type of ambulatory infusion device, the valve actuator is a common valve actuator that may switch the valve unit as common valve unit between the first filling state, the second filling state and the dosing state. While the before-described type of embodiment is favorable with respect to the functional and fluidic separation of components associated with the infusion of the first and second drug respectively, the second further embodiment is favorable regarding the costs and compactness, since the (typically disposable) reservoir and valve unit, as well as the valve actuator and reservoir actuator, are shared. In a further type of embodiment, a common reservoir is present as discussed before, while the fluidic coupling to the patient is realized separately. Here, the valve unit may have five different states, namely a first inlet state where the first container couples with the common reservoir via a first inlet port; a second alternative inlet state the second container couples with the with the common reservoir via a second inlet port; a first alternative dosing state where the common reservoir couples to a first infusion site interface via a first dosing port, a second alternative dosing state where the common reservoir couples to a separate second infusion site interface via a second dosing port. Like other embodiments, this type of embodiment may be extended to another number of, e.g., three or more drugs, with a separate inlet and dosing port being present for each of the drugs.

In some embodiments, the containers are typically but not necessarily cylindrical cartridges, typically a medical grade glass or plastic glass cartridge, with a sealing displaceable cartridge piston that is displaced inside the cartridge body when emptying the container. It is known that the cartridge piston, typically a rubber piston, of such drug cartridges tends to stick if it is not moved, in particular, displaced for a longer time period, and subsequently requires a considerable break-loose force. In the context of the here-assumed architecture with containers and one or more reservoirs, the cartridge piston moves only for the refilling of the reservoir. Depending on the user's individual therapy demands, the time period between consecutive refilling operations may be comparatively long, typically several hours, up to a day or more. It is further to be understood that, when refilling the reservoir, drug is sucked out of the container and the cartridge piston moves only via a pulling force as a result of the sucking pressure that is exerted by the drug on its liquid-contacting front surface. Favorably, no or only little additional pushing force is applied on the cartridge piston. It is further to be understood that the required break-loose force to overcome the sticking may be in the same range or even be larger than the maximum force that can be applied by the sucking pressure. Consequently, sticking is an issue of concern.

In a further aspect, the before-explained problem of a sticking cartridge piston is reduced and favorably avoided. This may be achieved by a piston sticking prevention method. The piston sticking prevention method includes, in the dosing state, comparing the time that has lapsed since the refilling of the reservoir with a pre-determined back-dosing time interval. The piston sticking prevention method further includes, if it is determined that the back-dosing time interval has lapsed, controlling a valve actuator to switch the valve unit from the dosing state into the filling state, followed by controlling the reservoir actuator to decrease the fluidic volume of the reservoir by a back-dosing volume, followed by controlling the valve actuator to switch the valve unit back from the filling state into the dosing state. According to a further aspect, the problem of preventing sticking of a cartridge piston is solved by an ambulatory infusion device control unit that is configured to execute a piston sticking prevention method.

By decreasing the fluidic volume of the reservoir, an amount of drug that corresponds to the back-dosing volume is forced from the reservoir into the container. In this process, a pushing force is accordingly exerted by the drug onto the cartridge piston, thereby overcoming the sticking friction and the break-loose force. It is noted that during the back-dosing, no drug is infused into the patient's body. The back-dosing volume is comparatively small, e.g., in a range of 1 IU to 5 IU. The back-dosing time interval is favorably somewhat shorter than a time interval beyond which sticking can be expected to occur and may, for example, be 12 hours in an exemplary embodiment.

The piston sticking prevention method may be carried out repeatedly or continuously in parallel and independent from the method for scheduling the refilling. In alternative embodiments, however, it may be carried out in a coordinated way with the method for scheduling the refilling. It may in particular be carried out if it is determined that the reservoir shall not be refilled at the present point in time.

It is noted that the disclosed sticking-friction prevention method is in principle independent and distinct form the refilling scheduling method and may optionally be implemented and carried out without some or all of the other method steps. Similarly, an ambulatory infusion device control unit may be configured to execute a sticking-friction prevention method, without being necessarily configured to carry out all or some of the steps of the method for scheduling the refilling of the reservoir.

A piston sticking prevention method as explained before may be applied to some or all containers, in particular a first and a second container.

In a further aspect, a computer program product including a non-transient computer readable medium can be provided. The non-transient computer readable medium has stored therein computer program code configured to direct a processor to execute a method according to any embodiment as discussed above and/or further below, and/or to act as refilling scheduling unit and/or as ambulatory infusion device control unit according to any embodiment as discussed above and/or further below. The processor may in particular be realized or may be formed by one or more microprocessors and/or microcontrollers.

In a further aspect, the ambulatory infusion device includes an ambulatory infusion device control unit as discussed above. The ambulatory infusion device further includes a first valve actuator in operative coupling with the first valve control unit and a second valve actuator in operative coupling with the second valve control unit. The ambulatory infusion device further includes a first reservoir actuator in operative coupling with the first reservoir actuator control unit and a second secondary actuator in operative coupling with the second reservoir actuator control unit. The valve actuators and the reservoir actuators are typically electrical actuators such as rotary actuators, in particular DC motors, brushless DC motors or stepper motors. Other types of electric actuators may also be used, in particular shape memory alloy actuators as valve actuators. The valve actuators are designed to releasably operatively couple and engage the associated valve units. The reservoir actuators are each designed to releasably operatively couple and engage a piston that is received in a dosing cylinder as explained below, with the piston and the dosing cylinder forming a metering pump unit. The metering pump unit and the valve unit form, in combination, a dosing unit and are realized as a common integral unit. A dosing cylinder and its piston further form a reservoir of controlled variable volume.

In a further type of ambulatory infusion device, a single valve actuator and a reservoir actuator is present that is designed to couple with a common reservoir as explained before and further below.

The reservoir actuator or reservoir actuators of the ambulatory infusion device as well as the corresponding reservoir actuator control units are favorably designed to increase and/or decrease the volume of the reservoir or reservoirs in a metered, i.e., volumetrically controlled way and to, in particular, decrease the fluidic volume in a number of incremental steps of defined volume and over an extended period of time.

Generally, a method in accordance with any disclosed embodiment may be carried out by way of a corresponding embodiment of a refilling scheduling unit, ambulatory infusion device, ambulatory infusion device control unit and/or a computer program product, which is accordingly also disclosed. Similarly, refilling scheduling units, ambulatory infusion device control units, ambulatory infusion devices and computer-program products in accordance with disclosed embodiments may be used to carry out a corresponding method embodiment, which are accordingly also disclosed.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
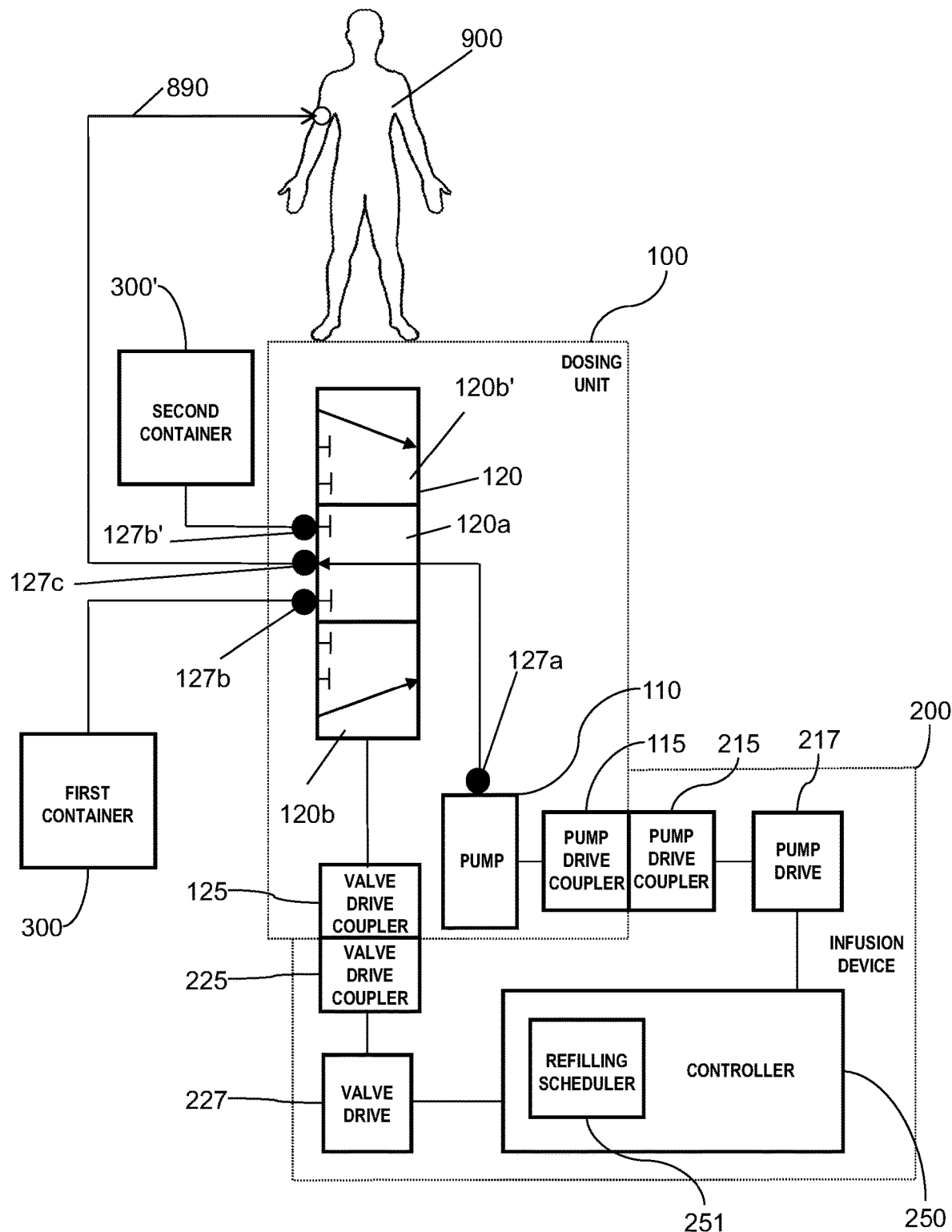
FIG. 1 shows major components of an ambulatory infusion system in a simplified functional view.

In the following, reference is first made to FIG. 1. FIG. 1 shows a dosing unit 100, an ambulatory infusion device 200, and a first drug reservoir 300 (also referred to as "first container") and a second drug reservoir 300' (also referred to as "second container"). In an example that is also assumed in the following, the first container 300 stores insulin and the second container 300' stores glucagon, both in the form of a liquid formulation. It is to be noted that only those structural and functional units are shown that are of particular relevance in the context of the present disclosure.

The dosing unit 100 includes a metering pump unit 110, including a dosing cylinder with a bore and a piston (elements not separately referenced) as described above in the general description. In a proximal front wall of the dosing cylinder, a bore is arranged as fluidic port that couples to the pump port 127a. The dosing unit further includes a valve unit 120 that may alternatively be in a first filling state, 120b, a second filling state 120b', or a dosing state 120a. During operation, the valve unit 120 is repeatedly switched between those states as explained further below in more detail. The first container 300 is fluidically coupled to the valve unit 120 via a first filling port 127b and the second container 300' is fluidically coupled to the valve unit 120 via a second filling port 127b' that is different from the first filling port 127b. The patient 900 is fluidically coupled to the valve unit via a dosing port 127c and infusion site interface 890, which may optionally be integral with a fluidic line, e.g., a catheter. The dosing unit 100 further includes a valve driver coupler 125 for switching the valve unit 120 between the first filling state 120b, the second filling state 120b', and the dosing state 120a. Similarly, the dosing unit 100 includes a pump driver coupler 115 for moving the piston of the pump unit 110 linearly inside the dosing cylinder. In an exemplary embodiment, the maximum filling volume of the dosing cylinder is 7 IU (International Units) of a liquid insulin formulation with concentration U100, respectively 70 microliter.

With respect to the valve unit 120, it is further noted that FIG. 1 only shows the states 120a, 120b, 120b' where either of the filling ports 127b, 127b' or the dosing port 127c is coupled to the pump port 127a. In a further optional intermediate state, however, all ports 127a, 127b, 127b', 127c may be closed, resulting in fluidic isolation.

The ambulatory infusion device includes a pump drive 217 that is coupled to a pump drive coupler 215 as well as a valve drive 227 that is coupled to a valve drive coupler 225. The pump drive 217 and the valve drive 227 are powered and controlled by an electronic ambulatory infusion device control unit 250 that is typically based on one or more microcontrollers and/or microprocessors.

The dosing cylinder and the piston form in combination a common reservoir, while the drug reservoir 300 forms a first container and the second drug reservoir 300' forms a second container as explained above. The first container 300 and the second container 300' may be realized by a cylindrical cartridge with sealing displaceable cartridge piston, or may be a fully or partly flexible container, such as a pouch. The first container 300 and the second container 300' may further be of identical or different design. Further, either of them may be provided readily filled by a manufacturer, or may be user-filled. The ambulatory infusion device control unit 250 further includes a reservoir actuator control unit (not separately referenced) that controls operation of the pump drive 217 as reservoir actuator. Further, the ambulatory infusion device control unit 250 includes a valve actuator control unit (not separately referenced) that controls operation of the valve drive 227 as valve actuator. The ambulatory infusion device control unit 250 further includes a refilling scheduling unit 251 in accordance with the present disclosure, operation of which is further explained in more detail below.

It is noted that the containers 300, 300' and the dosing unit 100 are shown as distinct from the ambulatory infusion device 200. They may be and typically are, however, in an operational configuration mechanically coupled to the ambulatory infusion device 200 to form a common, compact unit, and/or may be inserted into corresponding compartments of the ambulatory infusion device housing. Further, the dosing unit 100 and either or both of the containers 300, 300' may be realized as common unit in some embodiments.

Favorably, the ambulatory infusion device is designed as patch device that is designed to be, in a situation of use, directly attached to the body of the patient 900, e.g., the abdomen as generally known in the art. This has the advantage that the fluidic volume of the infusion site interface 890 is small and preferably negligible. A negligible fluidic volume of the infusion site interface is favorable in view of the required switching between the infusion of insulin and glucagon, or, more generally, the first and second drug. If the fluidic volume is not negligible, it may be considered as explained further below.

Figure 2:
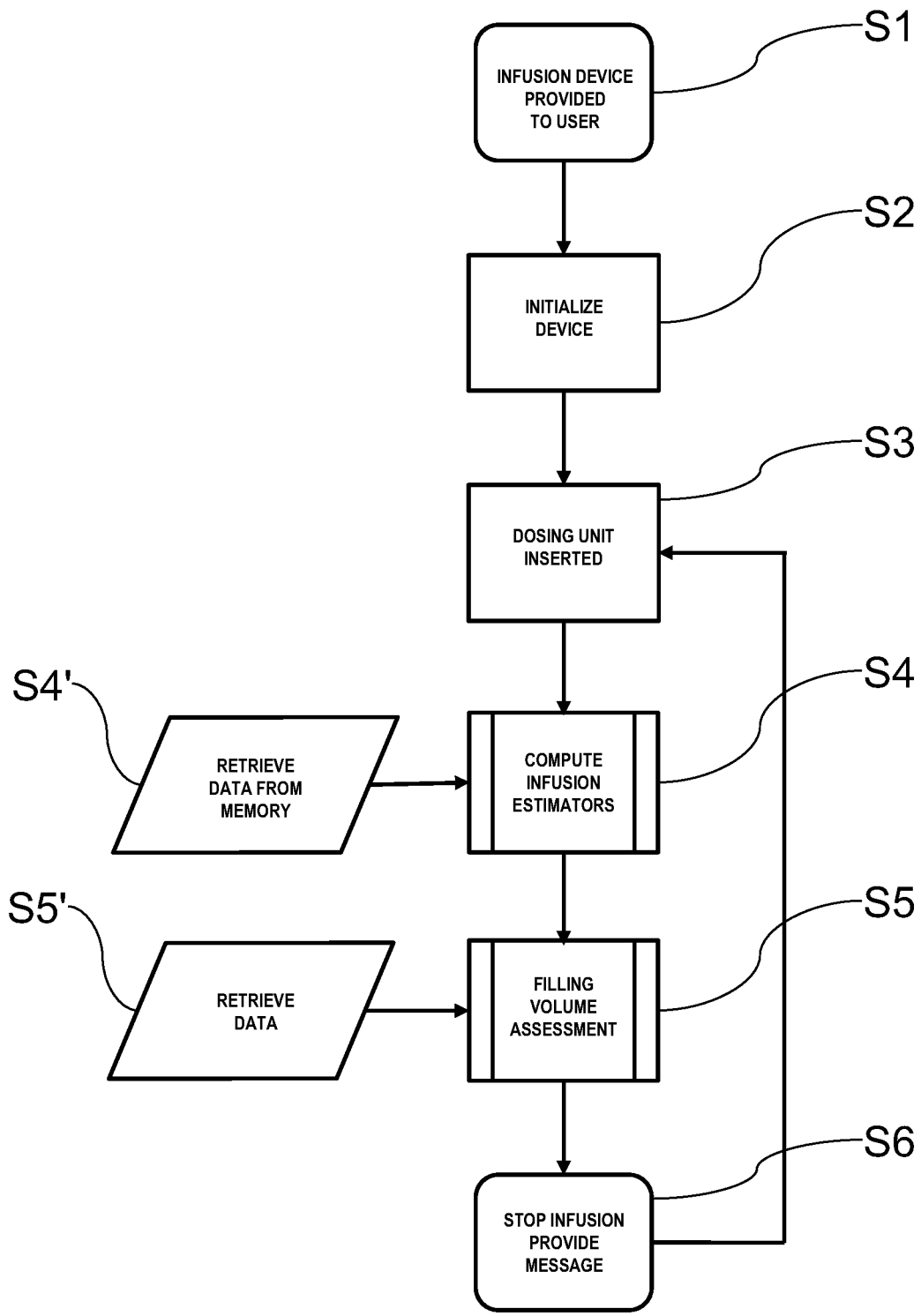
FIG. 2 shows an operational flow in accordance with the present disclosure.
Figure 3:
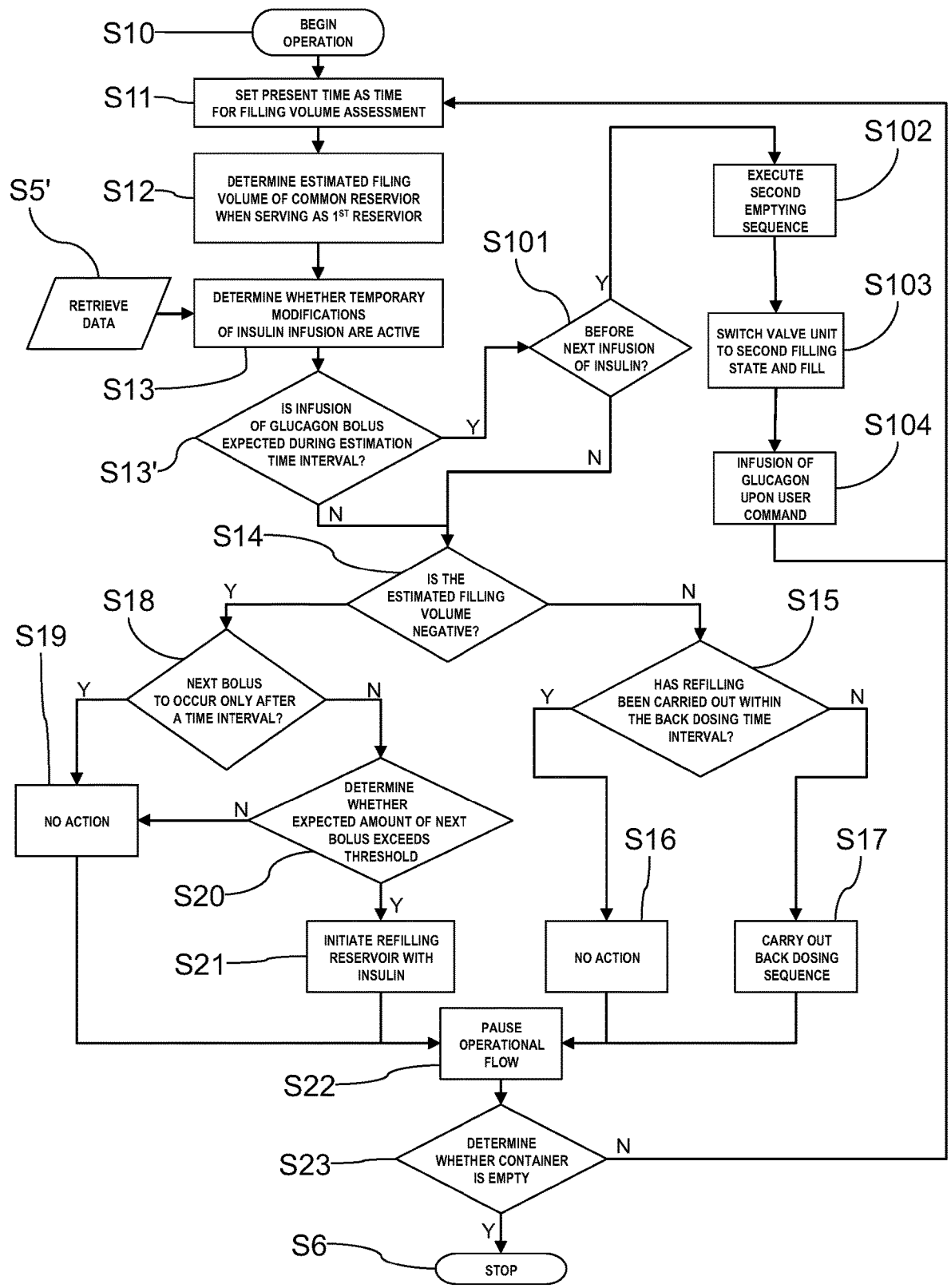
FIG. 3 shows a further operational flow of a refilling scheduling method in accordance with the present disclosure.

In the following, reference is additionally made to FIG. 2, illustrating an exemplary method in accordance with the present disclosure. The method starts in step S1 where a new ambulatory infusion device is provided to a user, e.g., a Person with Diabetes (PwD). The ambulatory infusion device is designed to be used in combination with a first and second container and a common reservoir (referred to as "reservoir") as explained before. It is noted that the methods that are illustrated in FIGS. 2, 3 are based on a setup with an ambulatory infusion device 200 and a dosing unit 100 and its components as illustrated in FIG. 1 and explained before.

In subsequent parameter setting step S2, the ambulatory infusion device is prepared and initialized for use by the user. This in particular includes the programming of the basal administration schedule for insulin as first drug, or a number of basal administration schedules, e.g., for working days and for weekends, as explained before. In many state-of-the-art systems, the ambulatory infusion device comprises or is adapted to operatively couple to a bolus recommendation system. A bolus recommendation system is designed to compute and propose to the user bolus volumes of drug boli, in particular insulin boli, that are appropriate for covering an amount of food intake, in particular carbohydrate intake, and/or for lowering undesirably raised blood glucose values. The computation depends on the amount and potentially type of food and/or the blood glucose value, using a number of patient-specific bolus computation parameters that are also set respectively programmed in step S2. If the ambulatory infusion device that has been provided in step S1 is a replacement device for a previously used device, step S2 may comprise or consist of retrieving the one or more basal administration schedules and bolus computation parameters from the previously used device respectively from a data file storing such parameters.

In subsequent maintenance step S3, a dosing unit with a reservoir as well as a first container and a secondary container are inserted into the ambulatory infusion device and coupled with an infusion cannula directly or via infusion tubing. Further, additional steps that are required in the context of exchanging the dosing unit and/or the reservoir are carried out, such as priming. Here it is assumed that the both containers and the dosing unit with the reservoir are generally exchanged along with each other, e.g., every few days up to every few weeks, in dependence of the user's individual requirements. The dosing unit and the containers may also be formed as common integral unit. Alternatively, however, they may be structurally separate and also exchanged separate from each other. Further, glucagon as second drug may be infused in substantially lower volumes as compared to the first drug insulin. Therefore, it may be foreseeable to replace the first and second container independent from each other.

In subsequent step S4, standard infusion estimators are computed for use during regular operation. The standard infusion estimators include a set of set of first standard infusion estimators for insulin and a set of second standard infusion estimators for glucagon. The set of first standard infusion estimators includes a set of standard basal infusion estimators and a set of standard bolus infusion estimators. Since glucagon as second drug is only infused in the form of boli, the set of second standard infusion estimators only considers bolus infusion. By way of example, the estimation time interval is pre-determined as two hours, and a standard bolus estimator and a standard basal estimator for insulin as well as a standard bolus estimator for glucagon are computed for specific times of day with an interval of 10 minutes, that is, for 0:00 (midnight), 0:10, 0:20, 0:30, 0:40, 0:50, 1:00 (1 am), and so forth. The set of standard basal infusion estimators for insulin is computed based on the basal infusion schedule. Alternatively to a computation based on the basal infusion schedule as programmed, the basal infusion estimators may be computed based on actual past basal insulin infusion as stored in a history memory. This approach has the advantage that typical temporary modifications that occurred in the past are also taken into account. The set of standard bolus infusion estimators for insulin is computed based on a history of actual past bolus infusions that is stored in a history memory of the ambulatory infusion device itself and/or an external device, such as a remote controller or diabetes management device. For the computation, the data are retrieved from the history memory (Step S4'). For each time of day as start time for which the computation is carried out, the corresponding bolus infusion estimator is computed as, e.g., $80^{th}$ percentile, as explained above. The computation is, e.g., carried out based on a number of, e.g., three or seven past days. The standard bolus infusion estimators for glucagon are computed according to the same principles as the standard bolus infusion estimators for insulin.

Subsequent to steps S4, S4', regular drug infusion is carried out. As background process, a filling volume assessment procedure is repeatedly and automatically carried out (Steps S5, S5'), as explained further below in more detail.

If, during regular operation, either of the containers becomes empty, the operational flow proceeds with step S6 where infusion is stopped and a corresponding message is provided. From step S6, the operational flow returns to the maintenance routine S3. Favorably, one or more warnings are provided well before the container is actually empty, allowing the user to go to the maintenance step S3 and exchange the dosing unit and the containers at a convenient point in time.

In the following, reference is additionally made to FIG. 3, showing the operational flow of steps associated with the scheduling of the refilling, as well as a further related step during regular operation of the ambulatory infusion device.

In step S10, regular operation of the ambulatory infusion device is started for infusion of insulin as first drug, i.e., the ambulatory infusion device is operated to autonomously infuse insulin according to the basal administration schedule and additional insulin boli on demand.

In subsequent step S11, the present point in time is set as time for carrying out a filling volume assessment. In subsequent step S12, the estimated filling volume of the common reservoir is determined, with the common reservoir serving as first reservoir.

In embodiments where sets of standard bolus infusion estimators for insulin and glucagon and standard basal infusion estimators for the insulin infusion have been computed in advance, step S12 comprises retrieving the standard basal infusion estimator and the standard bolus estimators that are associated with the present point in time and determining the estimated filling volume of the reservoir by subtracting the standard basal estimator and the standard bolus estimator for insulin from the current filling volume of the reservoir. In alternative embodiments where no standard infusion estimators have been computed in advance, the estimated filling volume of the reservoir may be computed in step S12 as explained in the general description, using the present point in time as the start point and the present point in time plus the estimation time interval as the end time.

In subsequent step S13, it is determined whether any temporary modifications of the insulin infusion are active. Data regarding such temporary modification may be retrieved (step S5') from a continuous glucose measurement device or continuous glucose measurement unit, and/or from a memory of the ambulatory infusion device which stores information regarding temporary modifications. If such modification is active, step S13 further includes modifying or updating the estimated filling volume of the reservoir accordingly.

In subsequent step S13', it is determined whether the infusion of a glucagon bolus is expected to occur in the estimation time interval between the present point in time and the future point in time and the operational flow branches in dependence of the result. If no infusion of a glucagon bolus is expected, the operational flow proceeds with step S14 as explained further below.

If the infusion of a glucagon bolus is expected, the operational flow proceeds with step S101. In step S101, it is determined whether the infusion of the glucagon bolus is expected to occur before the next following infusion of an insulin bolus, or, alternatively, if the infusion of a glucagon bolus is expected before the next following insulin infusion, and the operational flow branches in dependence of the result. In a further general implementation of step S13' it is determined whether the next following infusion is expected to be an insulin or a glucagon infusion.

If it is determined in step S101 that the next following insulin infusion or insulin bolus infusion is expected to occur before the actual point in time of the glucagon infusion, the operational flow again proceeds with step S14. Otherwise, the operational flow proceeds with step S102. In step S102, a second emptying sequence is first carried out. In the second emptying sequence, the valve actuator is controlled to switch the valve unit into the first filling state, thereby fluidically coupling the dosing cylinder as common reservoir with the first container, followed by controlling the reservoir actuator to decease the fluidic volume of the dosing cylinder as common reservoir to a minimum volume. Thereby, the dosing cylinder is emptied of insulin. In embodiments where the fluidic volume of the infusion site interface 890 is not negligible, the second emptying sequence may include, prior to switching the valve unit form the dosing state into the first filling state, increasing the fluidic volume of the reservoir by withdrawing the piston in the dosing cylinder by the fluidic volume of the infusion site interface, thereby sucking the insulin that is present in the infusion site interface into the dosing cylinder respectively reservoir.

In subsequent step S103, the valve unit is controlled to switch the valve unit into the second filling state, thereby fluidically coupling the dosing cylinder as common reservoir with the second container that comprises glucagon. Further in step S103, the reservoir actuator is controlled to increase the fluidic volume of the dosing cylinder as reservoir, thereby filling the dosing cylinder with glucagon. The filling volume of glucagon favorably corresponds to the amount that is expected to be infused based on the bolus infusion estimator for glucagon.

In subsequent step S104, a specific user command for the glucagon infusion is awaited. Further in step S104, upon the glucagon infusion being commanded by the user, the valve actuator is controlled to switch the valve unit into the dosing state, followed by controlling the reservoir actuator to decrease the filling volume of the dosing cylinder as reservoir, thereby infusing the glucagon. Since the dosing cylinder has been filled with glucagon beforehand, the glucagon infusion can start immediately upon being commanded, which is particularly favorable. It is noted that the step of switching the valve unit into the dosing state could alternatively be done in step S103 after filling the dosing cylinder with glucagon. At the end of the glucagon infusion, the dosing cylinder is empty, i.e., the fluidic volume of the reservoir is minimum respectively zero or at least negligible. Subsequently, the operational flow returns to step S11 as explained before.

In embodiments where the ambulatory infusion device is operatively coupled with a continuous glucose sensor to operate as closed loop system, awaiting a specific user command for the glucagon infusion may not be required.

In a practical implementation, the sequence of steps S102, S013 and S104 that is directly related to the glucagon infusion as second drug may include a number of further steps and branches that are not reflected in FIG. 3 for the sake of clarity and conciseness. In particular, a situation may occur where a glucagon infusion that is expected based on the infusion history is in fact not carried out. In such situation, the operational flow may provide for forcing the glucagon back into the second container. Further, a situation may occur where the user decides to infuse glucagon, but with a different bolus volume than expected. If the actual bolus volume is smaller than expected, the dosing cylinder is not empty at the end of the glucagon infusion. In this case, step S104 may include switching the valve unit into the second filling state and forcing the remaining glucagon back into the second container. If the actually commanded bolus volume is larger than expected, the current filling volume may be infused in a first step, followed by filling the dosing cylinder with the remaining volume subsequently in a second step, or the filling volume of the dosing cylinder may first be increased to the desired volume and the glucagon infusion may be carried out in a single step.

In embodiments where the fluidic volume of the infusion site interface 890 is not negligible, step S104 may include, following the glucagon infusion, increasing the fluidic volume of the dosing cylinder as reservoir by withdrawing the piston in the dosing cylinder by the fluidic volume of the infusion site interface, thereby sucking the glucagon that is present in the infusion site interface into the dosing cylinder respectively reservoir, followed by switching the valve unit into the second filling state and forcing the glucagon into the second container.

In step S14, the operational flow branches in dependence of the estimated filling volume with insulin as the first drug.

If the estimated filling volume at the future estimation point in time is positive, the operational flow proceeds with step S15. Here it is accordingly assumed that the reservoir will not become empty within the estimation time interval. In this case, optional steps S15, S16, S17 are carried out.

In step S15, the time that has lapsed since the last refilling of the reservoir is assessed by way of comparison with a pre-determined back-dosing time interval of, e.g., 12 hours, and the operational flow branches in dependence of the result. If a refilling has been carried out within the back-dosing time interval, the operational flow proceeds with step S16 where no action is required. Otherwise, a back-dosing sequence is carried out in step S17.

In the back-dosing sequence, the valve actuator is controlled to switch from the dosing state into the filling state. Subsequently, the reservoir actuator is, while in the dosing mode, controlled to decrease the fluidic volume of the reservoir by a small back-dosing volume. Subsequently, the valve actuator is controlled to switch back from the filling state into the dosing state. By decreasing the fluidic volume of the reservoir, an amount of drug that corresponds to the back-dosing volume is forced from the reservoir into the container. For the container being a glass or plastic cartridge with a cartridge piston that is sealing and movable arranged in a glass cartridge body, this is associated with a forced movement of the cartridge piston inside the cartridge body against its regular movement direction for emptying the cartridge, the forced piston movement being associated with a pushing force that is exerted onto the cartridge by the drug. In this way, a breakaway force between cartridge piston and cartridge body that typically builds up if the piston is not moved for some time, is overcome. Such breakaway force may be considerable and well above a pulling force that may be fluidically exerted on the piston by drawing liquid out of the cartridge. It is noted that the method steps associated with the back-dosing may also be independently implemented as piston sticking prevention method.

After either of step S16 or step S17, the operational flow proceeds with step S22 as explained further below.

In alternative embodiments where the breakaway force is particularly low, or in embodiments where another type of container, such as a pouch, is used, steps S15, S16, and S17 may not be required.

If the estimated filling volume at the end time is negative, the operational flow proceeds, following step S14, with step S18. In step S18, it is determined whether a next following bolus infusion is expected to occur only after a time interval as defined by a bolus timeout threshold from the present point in time. The bolus timeout threshold may be 20 min in a specific example, but longer or shorter values may be used as well. In the affirmative case, the operational flow proceeds with step S19 where it is determined that no action is presently required. Otherwise, the operational flow proceeds with step S20 where it is determined whether the expected amount of the next following bolus exceeds a bolus volume threshold. Favorably, the bolus volume threshold is dynamically set to the present filling volume of the reservoir. In the negative case, the operational flow also proceeds with step S19. Otherwise, the operational flow proceeds with step S21 where a refilling of the reservoir with insulin is initiated.

After carrying out either of step S19 or step S21, the operational flow proceeds with step S22. In step S22, the operational flow pauses until the present point in time corresponds to the time for the next subsequent execution of the filling volume assessment routine. In subsequent step S23, it is determined whether the container is empty. In the affirmative case, the operational flow proceeds with step S6, where the algorithm terminates and a replacement routine for the container and optionally the dosing unit with the reservoir is initiated. In the negative case, the operational flow returns to step S11 for the next execution of the filling volume assessment routine.

It is noted that, like steps S15, S16 S17, the steps S18, S19 S20 are optional. Via steps S18, S19, an otherwise initiated refilling is avoided in situations where it may in fact be unnecessary due to typical variability in drug infusion, as explained in the general description. Via additional step S20, a refilling is avoided at the present point in time in situations where the next expected on-demand bolus may still be infused without prior refilling.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for managing refilling at least one reservoir of an ambulatory infusion system from a first container that stores a first drug and for managing refilling the at least one reservoir of the ambulatory infusion system from a second container that stores a second drug, the method including carrying out a filling volume assessment routine, comprising:
   (a) providing the at least one reservoir;
   (b) providing a processor configured to:
      determine expected infusion of the first drug and the second drug between the present time $t_p$ and the end of an estimation time interval $t_f$,
      based on the determined expected infusion of the first drug and the second drug, determine at $t_p$ if the at least one reservoir shall be refilled with the first drug and/or if the at least one reservoir shall be refilled with the second drug; and
   (c) refilling the at least one reservoir with the first drug and/or the second drug when it is determined at $t_p$ that the at least one reservoir shall be refilled with the first drug and/or the second drug;
   wherein the filling volume assessment routine includes determining a first estimated filling volume of the at least one reservoir with the first drug at $t_f$ and determining if the at least one reservoir shall be refilled with the first drug based on the first estimated filling volume.

2. The method according to claim 1, wherein the filling volume assessment routine includes determining that the at least one reservoir shall be refilled with the first drug if the first estimated refilling volume is below a first filling volume threshold.

3. The method according to claim 1, wherein the filling volume assessment routine includes determining the first estimated filling volume by subtracting a first infusion estimator from a first filling volume of the first drug in the at least one reservoir at tp, wherein the first infusion estimator is an estimator for the amount of the first drug that is expected to be infused between tp and tf.

4. The method according to claim 3, wherein the method includes computing a set of first standard infusion estimators, with each first standard infusion estimator being an estimator for an amount of first drug that is expected to be infused in an estimation time interval beginning at an associated pre-determined time of day, and storing the set of first standard infusion estimators in a memory, wherein the filling volume assessment routine includes retrieving from the memory the first standard infusion estimator that is associated with the time of day corresponding to $t_p$.

5. The method according to claim 1, wherein determining if the at least one reservoir shall be refilled with the first drug is based, at least in part, on a pre-determined first basal infusion schedule for the first drug.

6. The method according to claim 1, wherein determining if the at least one reservoir shall be refilled with the first drug is based, at least in part, on an expected amount of on-demand bolus infusion for the first drug between $t_p$ and $t_f$.

7. The method according to claim 1, wherein the method includes computing a set of second standard infusion estimators, with each second standard infusion estimator being an estimator for an amount of second drug that is expected to be infused in an estimation time interval beginning at an associated pre-determined time of day, and storing the set of second standard infusion estimators in a memory, wherein the filling volume assessment routine includes retrieving from the memory the second standard infusion estimator that is associated with the time of day corresponding to $t_p$.

8. The method according to claim 1, wherein the at least one reservoir comprises separate first and second reservoirs.

9. The method according to claim 1, wherein the at least one reservoir comprises a single common reservoir configured to alternately receive the first drug and the second drug.

10. The method according to claim 9, wherein the filling volume assessment routine includes determining that the common reservoir shall be refilled with the second drug if an infusion of the second drug is expected to occur between $t_p$ and $t_f$ and prior to a next following on-demand bolus infusion of the first drug.

11. A refilling scheduling unit configured to carry out the method according to claim 1.

12. A non-transient computer readable medium having stored thereon computer program code configured to direct a processor to execute a method according to claim 1 and/or to act as a refilling scheduling unit and/or as an ambulatory infusion device controller.

\* \* \* \* \*